(12) United States Patent
Woods et al.

(10) Patent No.: US 11,963,877 B2
(45) Date of Patent: *Apr. 23, 2024

(54) ORTHOPAEDIC PROSTHESIS HAVING SUPPORT STRUCTURE

(71) Applicant: DEPUY SYNTHES PRODUCTS, INC., Raynham, MA (US)

(72) Inventors: Sherrod A. Woods, Fort Wayne, IN (US); Said T. Gomaa, Fort Wayne, IN (US); William Muhammad, Warsaw, IN (US); Bernice A. Gatrell, Columbia City, IN (US); Venkat S. Narayan, Fort Wayne, IN (US); Fionnan A. McNamara, Carlow (IE); Edward P. Kavanagh, Mallow (IE)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 96 days.

This patent is subject to a terminal disclaimer.

(21) Appl. No.: 17/462,422

(22) Filed: Aug. 31, 2021

(65) Prior Publication Data
US 2021/0386550 A1 Dec. 16, 2021

Related U.S. Application Data

(63) Continuation of application No. 15/876,635, filed on Jan. 22, 2018, now Pat. No. 11,103,356.

(51) Int. Cl.
| | | |
|---|---|---|
| A61F 2/44 | (2006.01) | |
| A61B 17/16 | (2006.01) | |
| A61F 2/30 | (2006.01) | |
| A61F 2/36 | (2006.01) | |
| A61L 27/04 | (2006.01) | |

(52) U.S. Cl.
CPC ........ *A61F 2/3609* (2013.01); *A61F 2/30942* (2013.01); *A61F 2/3607* (2013.01); *A61F 2/3662* (2013.01); *A61F 2002/30948* (2013.01); *A61F 2002/365* (2013.01); *A61F 2/367* (2013.01); *A61F 2/3672* (2013.01); *A61F 2002/368* (2013.01); *A61L 27/04* (2013.01)

(58) Field of Classification Search
None
See application file for complete search history.

(56) References Cited

U.S. PATENT DOCUMENTS

| | | | | |
|---|---|---|---|---|
| 4,938,771 A | * | 7/1990 | Vecsei | A61F 2/367 |
| | | | | 623/23.15 |
| 6,206,924 B1 | * | 3/2001 | Timm | A61F 2/28 |
| | | | | 623/17.11 |

(Continued)

*Primary Examiner* — Ann Schillinger
(74) *Attorney, Agent, or Firm* — Barnes & Thornburg LLP

(57) ABSTRACT

A femoral orthopaedic prosthesis includes a metallic core extending from a proximal end to a distal tip. The metallic core includes a neck that is positioned at the proximal end and is configured to receive a prosthetic femoral ball. An elongated stem extends distally from the neck to the distal tip. The stem includes a proximal section extending distally from the neck, and a distal section that extends proximally from the distal tip. The elongated stem also includes a pair of spaced-apart beams that connect the proximal section to the distal section. An aperture is defined in the stem between the pair of spaced apart beams.

16 Claims, 9 Drawing Sheets

(56) References Cited

U.S. PATENT DOCUMENTS

| | | | |
|---|---|---|---|
| 6,641,616 B1 * | 11/2003 | Grundei | A61F 2/36 |
| | | | 623/26 |
| 8,430,930 B2 * | 4/2013 | Hunt | A61F 2/40 |
| | | | 623/17.11 |
| 8,585,770 B2 * | 11/2013 | Meridew | A61F 2/4603 |
| | | | 623/23.46 |
| 9,186,252 B2 * | 11/2015 | Leibinger | A61F 2/28 |
| 9,421,108 B2 | 8/2016 | Hunt | |
| 9,456,901 B2 * | 10/2016 | Jones | C23C 4/02 |
| 9,545,317 B2 * | 1/2017 | Hunt | A61F 2/2846 |
| 9,549,823 B2 | 1/2017 | Hunt et al. | |
| 9,662,157 B2 * | 5/2017 | Schneider | A61F 2/44 |
| 9,895,231 B2 * | 2/2018 | Walter | A61F 2/3662 |
| 10,278,823 B1 * | 5/2019 | Xue | A61F 2/3662 |
| 11,103,356 B2 * | 8/2021 | Woods | A61F 2/30942 |
| 2006/0241776 A1 * | 10/2006 | Brown | A61B 17/7225 |
| | | | 623/32 |
| 2011/0264119 A1 * | 10/2011 | Bayon | A61L 27/24 |
| | | | 606/151 |
| 2011/0313532 A1 * | 12/2011 | Hunt | A61F 2/46 |
| | | | 623/18.11 |
| 2013/0123935 A1 * | 5/2013 | Hunt | A61F 2/28 |
| | | | 623/61 |
| 2013/0218282 A1 | 8/2013 | Hunt | |
| 2016/0287389 A1 | 10/2016 | Hunt et al. | |
| 2017/0095337 A1 * | 4/2017 | Pasini | A61F 2/36 |

* cited by examiner

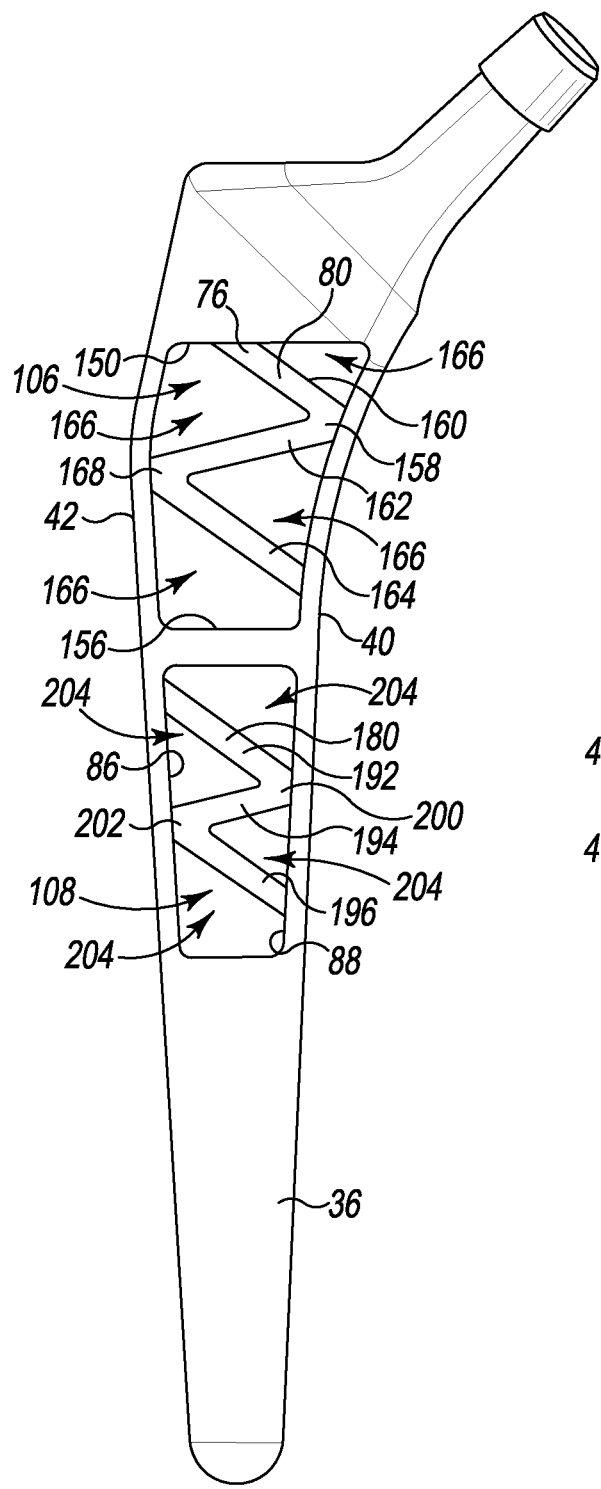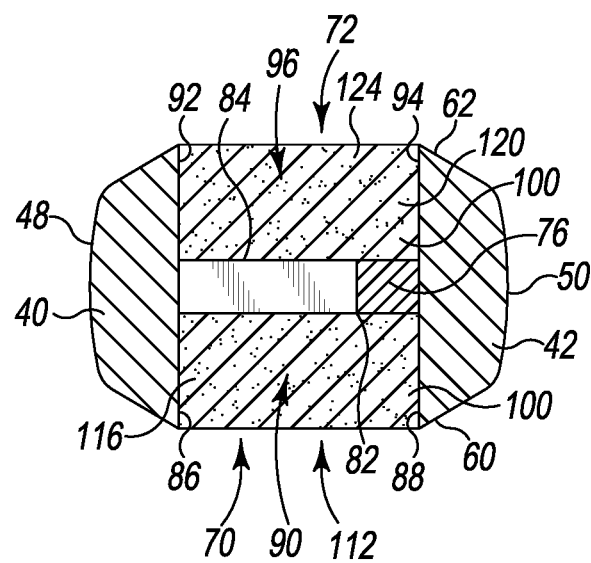
Fig. 4
Fig. 3

ORTHOPAEDIC PROSTHESIS HAVING SUPPORT STRUCTURE

This application is a continuation application of U.S. patent application Ser. No. 15/876,635, now U.S. Pat. No. 11,103,356, which was filed on Jan. 22, 2018 and is expressly incorporated herein by reference.

TECHNICAL FIELD

The present disclosure relates generally to orthopaedic prostheses, and particularly to orthopaedic prostheses for use in hip replacement surgery.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is received in the medullary canal of the patient's femur and a spherically-shaped head component that bears against the patient's acetabulum or a prosthetic replacement acetabular cup.

Femoral prostheses may be formed from metallic materials or a combination of metallic and polymeric materials. According to Wolff's law, a patient's bone tissue will remodel in proportion to the stress applied it. Because elongated stem components formed from metal typically have an elastic modulus greater than the elastic modulus of the patient's bone, metallic stem components may shield the patient's bone from stress such that the proximal femoral bone does not remodel to an effective degree, possibly resulting in a loss of support for the implant and/or implant failures.

Generally, increased stiffness in a prostheses may result in stress shielding around the prostheses, which results in poor bone growth and may cause loosening or fracturing of the prostheses. However, increased flexibility in the prostheses may result in reduced strength. Typically, a younger, more active person requires a more flexible prostheses to reduce stresses on the prostheses and promote bone growth. Conversely, an older, less active person may achieve bone growth with a stiffer prostheses that provides additional strength.

SUMMARY

According to one aspect of the disclosure, a femoral orthopaedic prosthesis is disclosed. The femoral orthopaedic prosthesis includes a metallic core extending from a proximal end to a distal tip. The metallic core includes a neck that is positioned at the proximal end and is configured to receive a prosthetic femoral ball. The metallic core also includes an elongated stem extending distally from the neck to the distal tip. The stem includes a proximal section extending distally from the neck and a distal section that extends proximally from the distal tip. A pair of spaced-apart beams connects the proximal section to the distal section, and an aperture is defined in the stem between the pair of spaced apart beams. The aperture extends through the stem from an anterior opening to a posterior opening. The stem also includes a cross-beam positioned in the aperture between the anterior and posterior openings.

It should be appreciated that the femoral orthopaedic prosthesis may be a customized patient-specific femoral orthopaedic prosthesis. According to another aspect of the disclosure, a method for designing a customized patient-specific femoral orthopaedic prosthesis is disclosed. The method includes acquiring one or more images of a patient's bone, simulating stresses on the bone to acquire bone data, modeling an implant based on the bone data, and simulating stresses on the implant model to acquire implant performance data. The bone data is compared to the implant performance data to determine whether the implant performance data matches the bone data. If it does not, the method may include additional steps to refine the design of the implant model to improve the implant performance.

In some embodiments, the cross-beam may be a plurality of cross-beams that extend between the pair of spaced-apart beams. A plurality of openings may be defined between adjacent cross-beams. Each cross-beam may extend obliquely relative to the other cross-beams of the plurality of cross-beams. Each opening of the plurality of openings may be triangular-shaped. Porous foam may be positioned in the aperture and extend through the plurality of openings. The porous foam may have an anterior surface that is substantially planar with an anterior surface of the stem, and a posterior surface that is substantially planar with a posterior surface of the stem.

In some embodiments, the pair of spaced apart beams may have a medial beam that defines a portion of the medial edge of the stem, and a lateral beam that defines a portion of the lateral edge of the stem.

In some embodiments, porous foam may be positioned in the aperture. The porous foam may have an anterior surface that is substantially planar with an anterior surface of the stem, and a posterior surface that is substantially planar with a posterior surface of the stem.

In some embodiments, the stem may have a central beam that extends between the pair of spaced-apart beams and separates the aperture into a first section and a second section. The central beam may have an anterior surface that is substantially planar with an anterior surface of the distal section of the stem, and a posterior surface that is substantially planar with a posterior surface of the distal section of the stem. The cross-beam may be a first cross-beam positioned in the first section of the aperture between the anterior and posterior openings. The stem may have a second cross-beam positioned in the second section of the aperture between the anterior and posterior openings.

In some embodiments, a first porous foam may be positioned in the first section of the aperture, and a second porous foam may be positioned in the second section of the aperture.

In some embodiments, a prosthetic femoral ball may have a distal opening sized to receive the proximal end of the metallic core.

According to yet another aspect of the disclosure, the femoral orthopaedic prosthesis includes a metallic core extending from a proximal end to a distal tip. The metallic core has a neck that is positioned at the proximal end and is configured to receive a prosthetic femoral ball. The metallic core also has an elongated stem extending distally from the neck to the distal tip. Porous foam is coupled to the metallic core. The stem includes a proximal section extending distally from the neck, and a distal section extends proximally from the distal tip. A pair of spaced-apart beams connects the proximal section to the distal section, and a cross-beam extends between the pair of spaced-apart beams. A first portion of the porous foam is positioned in an anterior notch that is defined between the proximal section, the distal section, the spaced-apart beams, and an anterior side of the cross-beam. A second portion of the porous foam is positioned in a posterior notch that is defined between the proximal section, the distal section, the spaced-apart beams, and a posterior side of the cross-beam.

In some embodiments, an opening may be defined through the cross-beam. The porous foam may extend through the opening defined through the cross-beam.

In some embodiments, the porous foam may have an anterior surface that is substantially planar with an anterior surface of the stem, and a posterior surface that is substantially planar with a posterior surface of the stem.

In some embodiments, the pair of spaced apart beams may have a medial beam that defines a portion of the medial edge of the stem, and a lateral beam that defines a portion of the lateral edge of the stem.

In some embodiments, the cross-beam may be a plurality of cross-beams that extend between the pair of spaced-apart beams. Each cross-beam may extend obliquely relative to the other cross-beams of the plurality of cross-beams.

In some embodiments, a prosthetic femoral ball may have a distal opening sized to receive the proximal end of the metallic core.

According to a further aspect of the disclosure, a method of designing a femoral orthopaedic prosthesis includes scanning a patient bone to generate a bone model. The method also includes simulating loads on the bone model to acquire bone data related to stresses on the patient bone. The method also includes producing a prosthesis model of an orthopaedic prosthesis based on the bone data. The method also includes simulating loads on the prosthesis model to acquire implant performance data related to stresses on the prosthesis model. The method also includes comparing the implant performance data to the bone data. The method also includes modifying the prosthesis model based on the comparison of the implant performance data to the bone data.

In some embodiments, modifying the prosthesis model may require at least one of adding or subtracting a cross-beam extending between a medial side and a lateral side of the prosthesis model. Modifying the prosthesis model may require at least one of adding or subtracting material from the cross-beam.

BRIEF DESCRIPTION

The detailed description particularly refers to the following figures, in which:

FIG. 3 is a cross-sectional view of the femoral orthopaedic prosthesis taken along line 3-3 in FIG. 1;

FIG. 4 is a side elevation of the femoral orthopaedic prosthesis shown in FIG. 1 with the porous foam removed;

DETAILED DESCRIPTION

Figure 1:
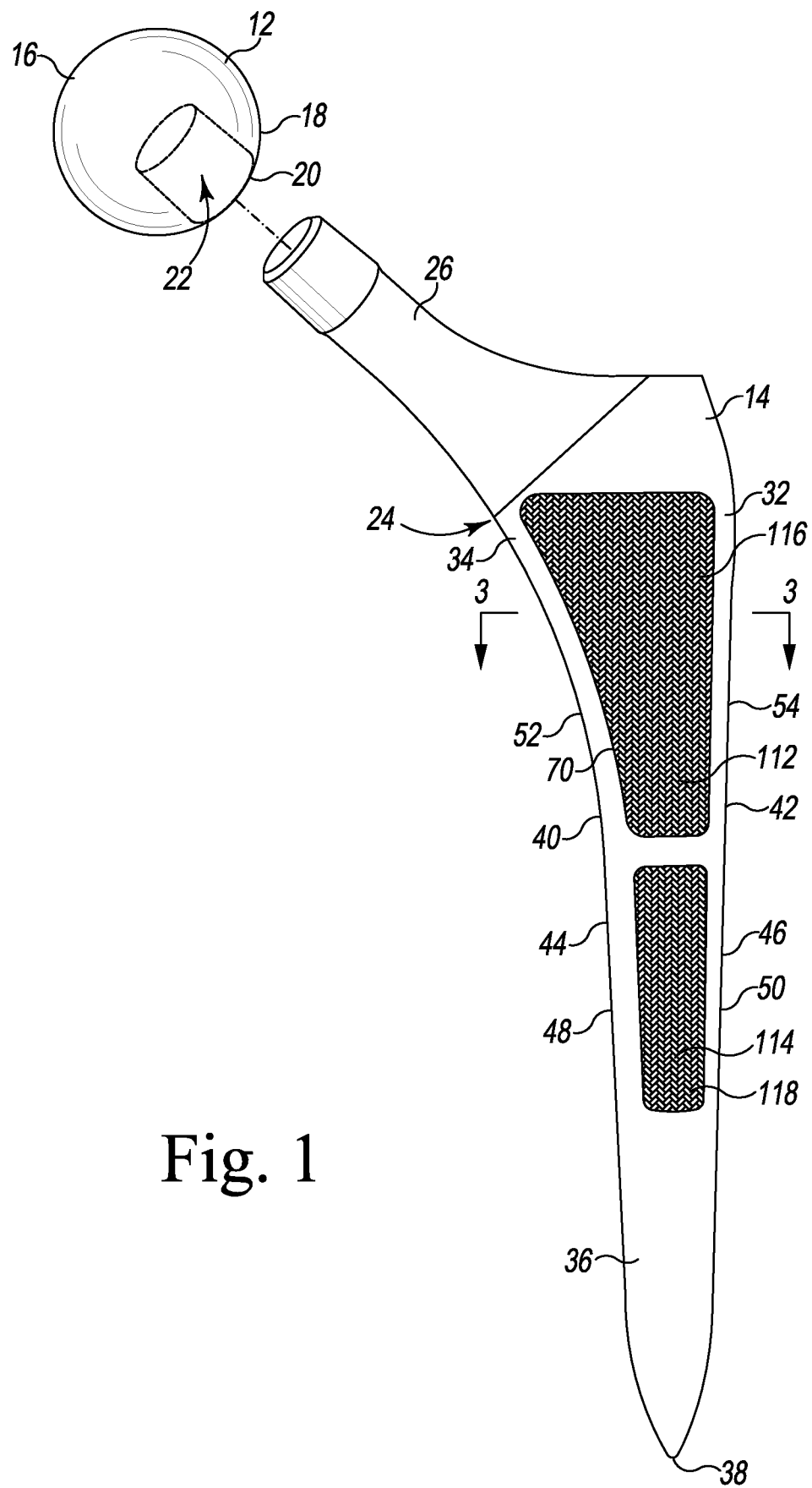
FIG. 1 is an exploded perspective view of a femoral orthopaedic prosthesis and a prosthetic femoral ball.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an orthopaedic prosthesis is illustratively embodied as a femoral orthopaedic implant 10 (hereinafter implant 10) of a hip prosthesis. The orthopaedic prosthesis is customized in the illustrative embodiment to provide a patient specific stiffness that balances the stiffness and strength to provide a stable orthopaedic prosthesis capable of supporting the patient and minimizing stress shielding around the implant. It should be appreciated that in other embodiments the orthopaedic prosthesis may be a generic implant, which is not patient-specific and is configured to balance the stiffness and strength under typical or average loads present in a variety of different patient hip joints.

The femoral orthopaedic implant 10 includes a head component 12 and an elongated stem component 14 that is configured to be inserted into an intramedullary canal of a patient's surgically-prepared femur (not shown). The head component 12 includes a spherical outer surface 16 configured to engage a patient's natural acetabulum (not shown) or a prosthetic acetabular cup implanted into the patient's pelvic bone. The head component 12 also includes a distal surface 18 having an opening 20 defined therein, and an inner wall (not shown) extends inwardly from the opening 20 to define an aperture 22 in the head component 12.

The stem component 14 of the implant 10 includes a core 24 having a neck 26 configured to be coupled to the head component 12. In the illustrative embodiment, the neck 26 is configured to be press-fit to a lining of the aperture 22 of the head component 12. It should be appreciated that in other embodiments the neck and the head component may be configured to be threaded, taper fit, or secured together by other fastening means.

The core 24 of the stem component 14 also includes a core body 32 extending distally from the neck 26. In the illustrative embodiment, the neck 26 and the core body 32 are formed as a monolithic structure (e.g., a single molded, cast, or three-dimensionally printed part). It should be appreciated that in other embodiments the neck 26 and the core body 32 may be formed as separate components secured to one another by a mechanical fastener (e.g., screw, bolt, taper fit, etc.), adhesive, or other suitable fastener.

The core body 32 lies generally in the coronal plane of a patient's body when the implant 10 is secured to the patient's femur. The core body 32 has a medial surface 48 and a lateral surface 50 that is positioned opposite the medial surface. Each of the surfaces 48, 50 are convex in the illustrative embodiment. When viewed in the coronal plane, a medial edge 44 is defined along the curved medial surface 48 and a lateral edge 46 is defined along the curved lateral surface 50. The core body 32 is tapered such that the thickness of the body 32 defined between the edges 44, 46 decreases along the length of the body.

Figure 2:
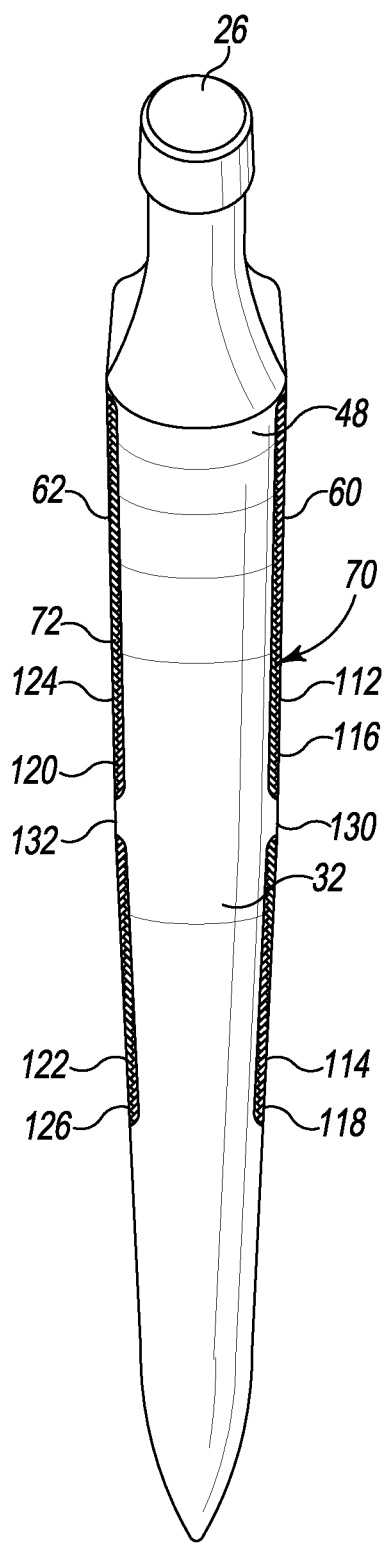
FIG. 2 is a front elevation view of the femoral orthopaedic prosthesis shown in FIG. 1.

Referring to FIG. 2, the core body 32 also includes an anterior surface 60 and a posterior surface 62 positioned opposite the anterior surface 60. In the illustrative embodiment, the anterior surface 60 and the posterior surface 62 extend between (and connect) the medial surface 48 and the lateral surface 50.

Returning to FIG. 1, the core body 32 of the core 24 extends from a proximal section 34 to a distal section 36 having a distal tip 38. The core body 32 also includes a medial beam 40, configured to be in compression when subjected to the loads present in the patient's joint, and a lateral beam 42, configured to be in tension when subjected to the loads present in the patient's joint, extend between and connect the proximal section 34 and the distal section 36. The lateral beam 42 is positioned opposite and spaced apart from the medial beam 40 such a portion 52 of a medial edge 44 is defined by the medial beam 40 and a portion 54 of the lateral edge 46 is defined by the lateral beam 42. The core body 32 also includes a central beam 110 that extends between the medial beam 40 and the lateral beam 42. The central beam 110 includes a distal sidewall 154 and a proximal sidewall 156. The central beam 110 also includes an anterior sidewall 130 and a posterior sidewall 132 (shown in FIG. 2).

Referring now to FIGS. 3-4, the core body 32 has an anterior opening 70 in its anterior surface 60 and a posterior opening 72 in its posterior surface 62. In the illustrative embodiment, an aperture 74 extends between the openings 70, 72 through the core body 32. The core body 32 includes a support structure 76 that cooperates with the medial beam 40 and the lateral beam 42 to define a truss structure, which, as described in greater detail below, is configured to provide a stiffness to the implant 10 that corresponds to a stiffness of a patient's bone while also providing the strength necessary to withstand the loads present in the patient's joints.

As shown in FIGS. 1 and 3, the aperture 74 is filled with porous foam 100 having a low elastic modulus. As used herein, a "low elastic modulus" refers to an elastic modulus or modulus of elasticity similar to that of a patient's natural femur (i.e., between 10 GPa and 20 GPa). In some embodiments, the porous foam 100 is formed from a foam matrix of titanium having an elastic modulus of approximately 10 GPa and an ultimate tensile strength of the foam matrix of titanium is approximately 35 MPa. In that way, the porous foam 100 has an elastic modulus that is closer to that of a patient's femur. It should be appreciated that in other embodiments the porous foam 100 may be formed any metallic foam matrix having a low elastic modulus, such as, for example, a CoCr foam matrix having an elastic modulus of approximately 19 GPa, a CoCr alloy foam matrix, a titanium foam alloy matrix, or other foam matrix. In further embodiments, the porous foam 100 is not metallic. The porous foam 100 has an anterior surface 102 and a posterior surface 104. The anterior surface 102 of the porous foam 100 is planar with the anterior surface 60 of the core body 32 and the anterior sidewall 130 of the central beam 110. The posterior surface 104 of the porous foam 100 is planar with the posterior surface 62 of the core body 32 and the posterior sidewall 132 of the central beam 110.

As shown in FIG. 4, the aperture 74 includes a proximal aperture section 106 and a distal aperture section 108 that are separated by the central beam 110. A portion 116 of porous foam 100 fills the proximal aperture 106, and a portion 118 of porous foam 100 fills the distal aperture 108. In other embodiments, the foam may extend over the central beam 110 such that an entire portion of the core body is encased within the foam.

As shown in FIGS. 3-4, the support structure 76 includes a cross frame 80 that is positioned in the proximal aperture section 74 and extends between the medial beam 40 and the lateral beam 42. The cross frame 80 includes a plurality of cross-beams 160, 162, 164 that extend at oblique angles relative to each other. The cross-beam 160 extends from an end attached to an inner sidewall 150 of the proximal section 34 of the core body 32 to an opposite end 158 attached to an inner sidewall 86 of the medial beam 40. The cross-beam 162 is attached to the cross-beam 160 and extends from the end 158 to another end 168 attached to an inner sidewall 88 of the lateral beam 42. The other cross-beam 164 of the cross frame 80 extends from the end 168 to an opposite end attached to the inner sidewall 86 of the medial beam 40. In the illustrative embodiment, the cross-beams 160, 162, 164, the medial beam 40, and the lateral beam 42 cooperate to form a truss configuration.

As shown in FIG. 4, a plurality of openings 166 are defined between the cross-beams 160, 162, 164. In the illustrated embodiment, each opening is substantially triangular in shape and filled with the porous foam 100. It should be appreciated that in other embodiments the openings may take other geometric forms.

As shown in FIG. 3, the cross-beams 160, 162, 164 define an anterior surface 82 of the cross frame 80 and a posterior surface 84 that is positioned opposite anterior surface 82. The sidewall 86 of the medial beam 40 and the sidewall 88 of the lateral beam 42 cooperate with the anterior surface 82 of the cross-beam 80 to define an anterior notch 90 of the aperture 74. The sidewall 86 of the medial beam 40 and the sidewall 88 of the lateral beam 42 cooperate with the posterior surface 84 of the cross-beam 80 to define a posterior notch 96 of the proximal aperture section 74.

The support structure 76 also includes a cross frame 180 that is positioned in the distal aperture section 108 and extends between the medial beam 40 and the lateral beam 42. The cross frame 180 includes a plurality of cross-beams 192, 194, 196 that extend at oblique angles relative to each other. The cross-beam 92 extends from an end attached to an inner sidewall 86 of the of the medial beam 40 to an opposite end 200 attached to an inner sidewall 88 of the lateral beam 42. The cross-beam 194 is attached to the cross-beam 192 and extends from the end 200 to another end 202 attached to the inner sidewall 88 of the lateral beam 42. The other cross-beam 196 of the cross frame 80 extends from the end 202 to an opposite end attached to the inner sidewall 86 of the medial beam 40. In the illustrative embodiment, the cross-beams 190, 192, 194, the medial beam 40, and the lateral beam 42 cooperate to form a truss configuration. A plurality of openings 204 are defined between the cross-beams 190, 192, 194. In the illustrated embodiment, each opening is substantially triangular in shape and filled with the porous foam 100. It should be appreciated that in other embodiments the openings may take other geometric forms.

Figure 5:
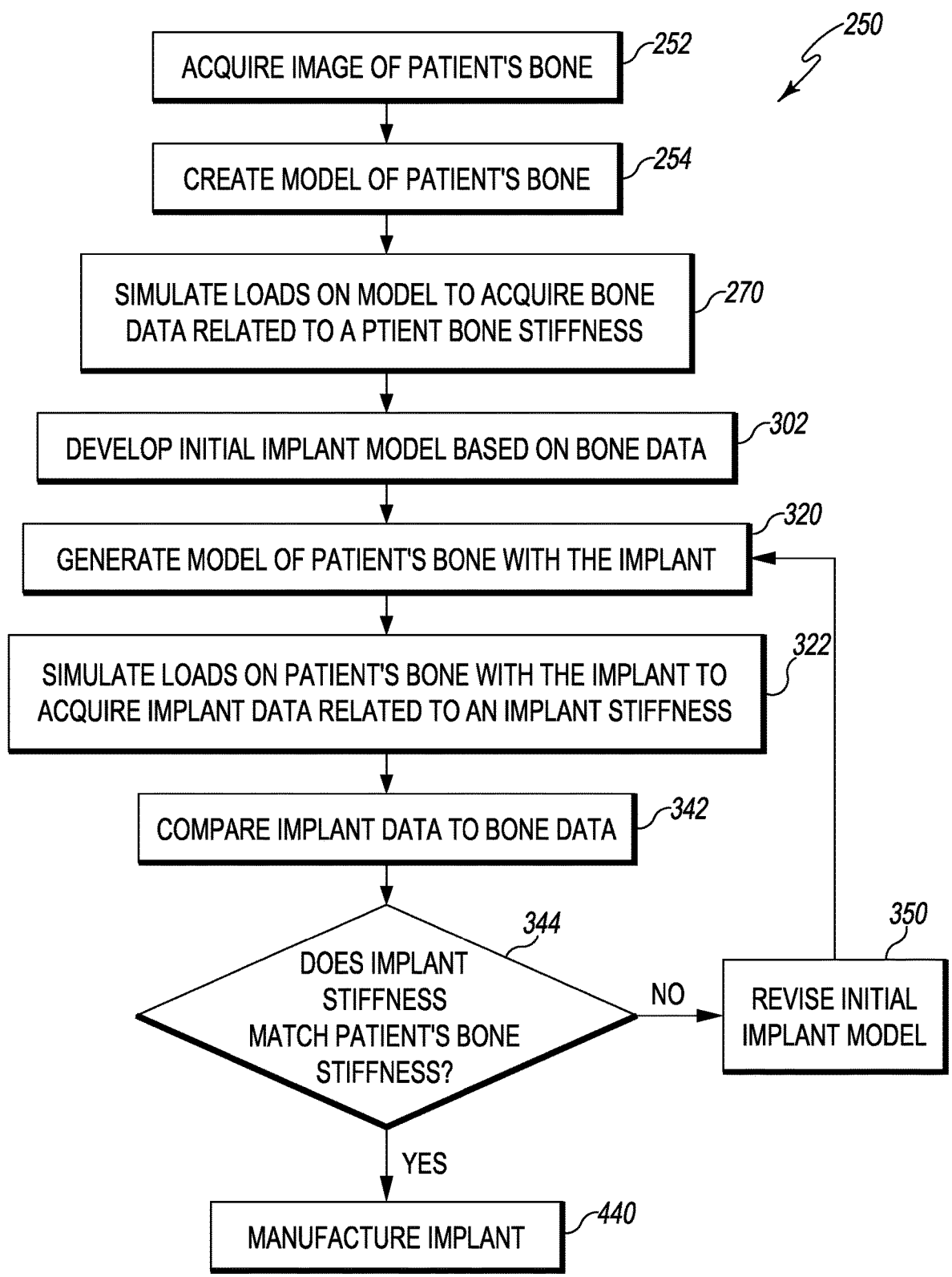
FIG. 5 is a flowchart of a routine for designing the femoral orthopaedic prosthesis shown in FIG. 1.

Referring now to FIG. 5, an exemplary flow chart of a routine 250 for designing the implant 10 includes a number of steps to size, shape, and produce a customized patient-specific orthopaedic prosthesis. It should be appreciated that the process for sizing, shaping, and producing generic orthopaedic prostheses may include many of the steps outlined in the routine 250, as described in greater detail below. The routine 250 illustratively begins at block 252 in which the patient's bones are scanned, for example, with x-ray, magnetic resonance imaging, computed tomography, or any other device. These scans produce images that may include three-dimensional images of that patient's bone or one or more two-dimensional images of the patient's bones that can be converted to a three-dimensional image. The routine 250 may then advance to block 254.

Figure 6:
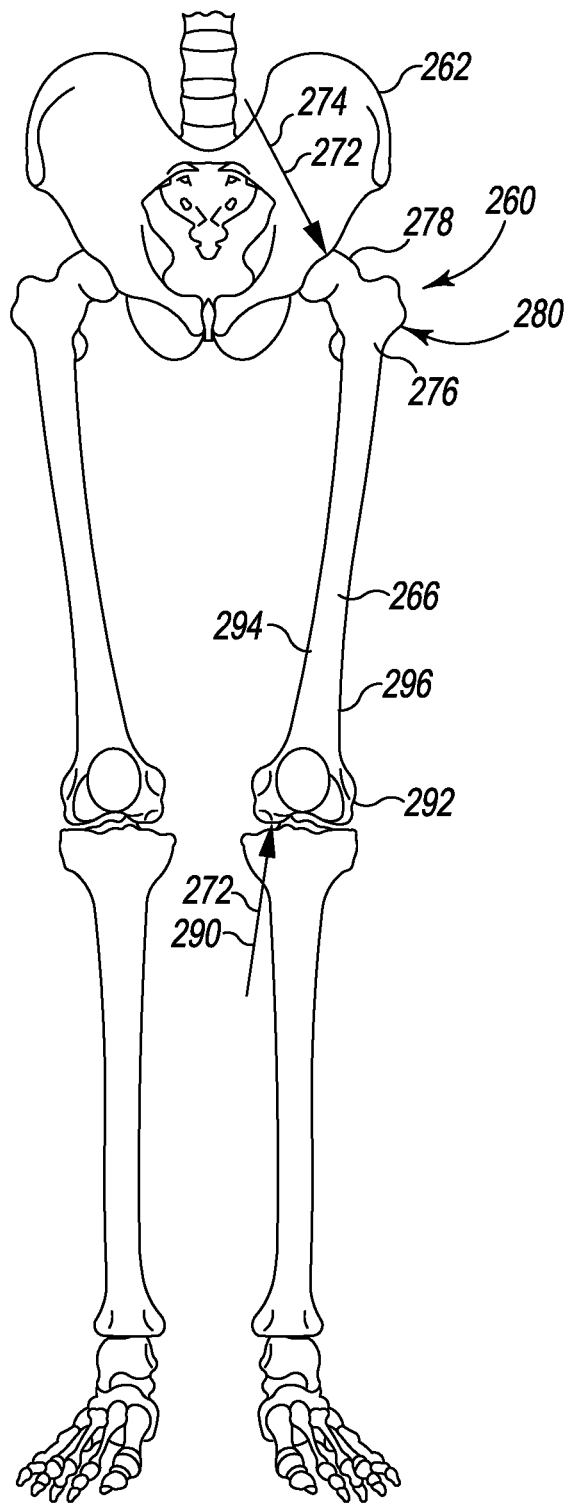
FIG. 6 is an illustration of a simulated 3-D bone model of a patient utilized in the routine illustrated in FIG. 5.

At block 254, a customized three-dimensional model 260 of the patient's bony anatomy is created. In some embodiments, the three-dimensional bony anatomy model may be created in a modeling program such as, for example, Materialise Mimics, which is commercially available from Materialise of Belgium. As shown in FIG. 6, the three-dimensional bony anatomy model 260 includes three-dimensional models of the patient's pelvis 262, patient's feet 264, patient's femur 266, and other bones of the patient's leg. In some embodiments, the customized three-dimensional bony anatomy model 260 may include only the patient's femur, and the models of the other bones may be taken from, for example, the AnyBody Managed Model Repository (AMMR), which commercially available from Anybody Technology of Denmark.

At block 270, the three-dimensional bony anatomy model 260 is load tested. Individual muscle forces, joint contact-forces and moments, and other aspects of the patient's anatomy are simulated to apply loads to the three-dimensional bony anatomy model 260. These loads and forces may be applied to the three-dimensional bony anatomy model 260 using, for example, the Anybody Modeling System, which is commercially available from Anybody Technology of Denmark. The simulated musculoskeletal loads and forces are scaled to match the patient's bony anatomy, and the loads may be calculated automatically by the software to apply various load conditions associated with specific activities, e.g. running or walking.

Load testing on the three-dimensional bony anatomy model 260 may also incorporate various patient specific factors. For example, the patient's bone type may be analyzed. Generally, the femur 266 may be normal, e.g. the lateral and medial edges have an even distribution of bone, or the femur 266 may be "stove-pipe" or "champagne flute" indicating that the medial and lateral edges narrow distally. Other factors to consider include the patient weight and age. Further, an activity level of the patient is considered while load testing. Based on the various factors, loads 272 are applied to the femur 266 in the three-dimensional bony anatomy model 260. The loads 272 include a hip load 274 that is applied to a proximal end 276 of the femur 266 through the acetabular cup 278 of the hip 280. A knee load 290 is applied to distal end 292 of the femur 266. The loads 272 are simulated in various conditions, e.g. standing still, walking, running, jumping, etc.

The loads 272 place the medial side 294 of the femur 266 in compression, while placing the lateral side 296 of the femur 266 is tension. Through the load testing, various stresses on the femur 266 of the three-dimensional bony anatomy model 260 are determined. For example, stresses on the proximal end 276, the distal end 292, the lateral side 296 and the medial side 294 may be determined. These stress may in turn be used to measure or calculate a stiffness of the three-dimensional bony anatomy model 260. Data related to the stiffness of the three-dimensional bony anatomy model 260 is stored as bone data.

With the data generated by load testing the three-dimensional bony anatomy model 260, the routine 250 may advance to block 302 in which an implant model is designed to provide a balanced stiffness that accounts for the stresses on the femur 266 to prevent stress shielding, while also providing a flexibility that prevents fracturing of the implant. Designing a patient specific implant model may include adding or subtracting cross-beams, increasing or reducing a thickness of the cross-beams, or increasing or decreasing a thickness of the lateral beam and/or medial beam.

At block 320, a virtual surgery may be performed on the femur model 266. During the virtual surgery, all of the resections and reaming to be performed during the orthopaedic surgery are simulated on the femur model 266. An intramedullary canal is also simulated in the femur model 266 so that the implant model can be virtually inserted into a surgically prepared femur model. In other embodiments, the prepared surfaces may be simply added to the three-dimensional bony anatomy model 260 without simulating the virtual surgery. The implant model may then be virtually inserted into the virtual surgically-prepared three-dimensional bony anatomy model 260.

The simulated load testing performed in block 270 may then be repeated with the implant model inserted into the virtual surgically prepared femur model at block 322 of the routine 250. While evaluating the strength of the implant, stresses on the proximal end 276, the distal end 292, the lateral side 296 and the medial side 294 are also calculated and the stiffness of the patient's bone with the implant model is determined. Data related to the stiffness of the patient's bone with the implant model is stored as implant performance data. The implant performance data is compared to the bone data, at block 342. For example, the stiffness of the implant model is compared to the stiffness of the bone model to determine whether the stiffness of the implant model matches the stiffness of the three-dimensional bony anatomy model 260 at block 344. In some embodiments, the stiffness of the implant model is considered a match if it is in a range of 60%-80% the stiffness of the three-dimensional bony anatomy model 260.

Figure 8:
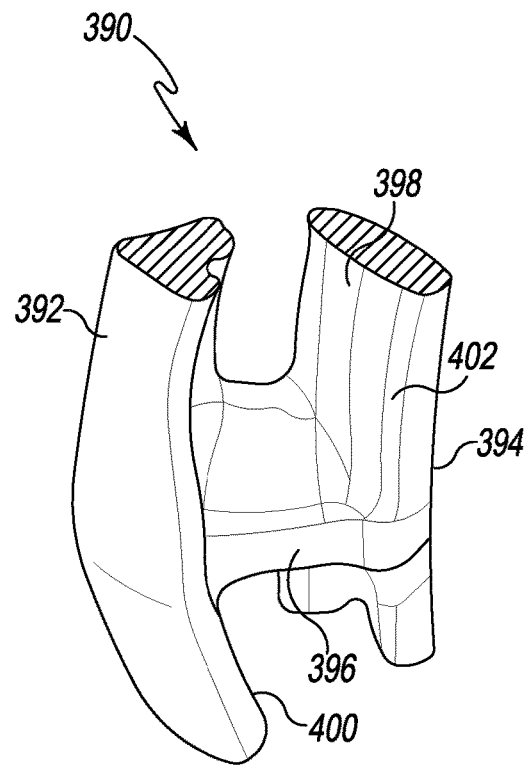
FIG. 8 is a perspective view of a portion of another femoral orthopaedic prosthesis.
Figure 9:
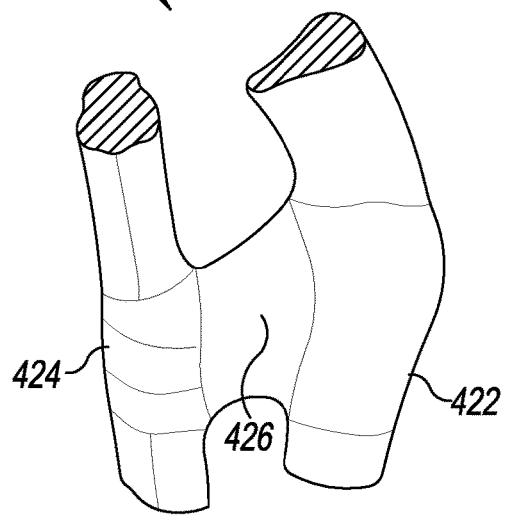
FIG. 9 is a perspective view of a portion of yet another femoral orthopaedic prosthesis.

If the stiffness of the implant model does not match the stiffness of the three-dimensional bony anatomy model 260, the implant model may be revised at block 350. Revisions to the implant model may include, for example, adding or subtracting cross-beams from the model to increase or decrease the stiffness as needed. The revisions may also include removing material from the implant model or gusseting the implant model, as shown in FIGS. 7-9.

Figure 7:
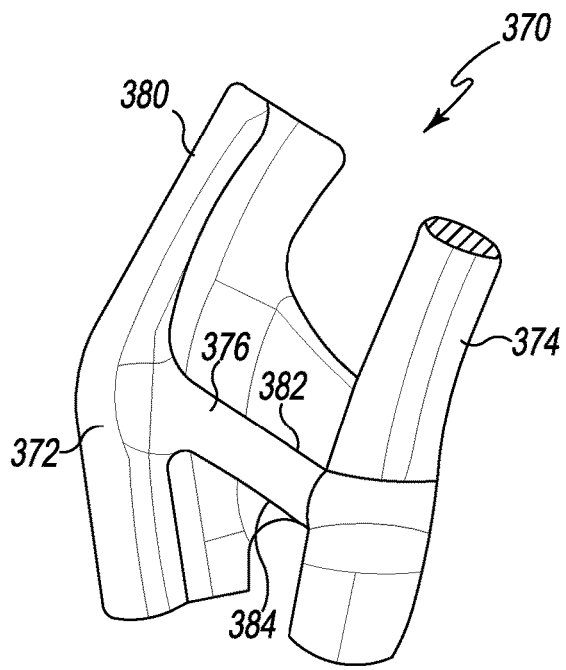
FIG. 7 is a perspective view of a portion of a femoral orthopaedic prosthesis.

For example, as shown in FIG. 7, one implant model 370 includes a medial beam 372, a lateral beam 374, and a cross-beam 376 extending between the medial beam 372 and the lateral beam 374. In the implant model 370, material has been added to a lateral surface 380 of the medial beam 372 and both a proximal surface 382 and a distal surface 384 of the cross-beam 376 to increase a stiffness of the implant model 370. Referring now to FIG. 8 another implant model 390 having a medial beam 392, a lateral beam 394, and a cross-beam 396 extending between the medial beam 392 and the lateral beam 394 is shown. Material has been added to a medial surface 398 of the lateral beam 394, a lateral surface 400 of the medial beam 392, and a proximal surface 402 of the cross-beam 396 to increase a stiffness of the implant model 390. FIG. 9 illustrates another implant model 420 having a medial beam 422, a lateral beam 424, and a cross-beam 426 extending between the medial beam 422 and the lateral beam 424. Material has been added to each of the medial beam 422, the lateral beam 424, and the cross-beam 426 to change the stiffness. After modifying the implant model, the implant model is tested again, at block 322.

If the stiffness of the implant model matches the stiffness of the three-dimensional bony anatomy model 260, the implant 10 may be manufactured based on the implant model, at block 440. In some embodiments, the implant 10 is manufactured utilizing additive manufacturing. In other embodiments, any form of manufacturing may be utilized to manufacture the implant 10. During manufacturing of the implant 10, the porous foam 100 is added as described above. The porous foam 100 is selected to have a porosity between 200 microns and 800 microns. The porosity is selected based on an age of the patient. For example, older patients may require a higher porosity to promote bone growth.

As described above, the orthopaedic prosthesis may be a generic implant that is not patient-specific. For example, the implant 10 may be designed using a pre-developed generic three-dimensional bony anatomy model from, for example, the AnyBody Managed Model Repository (AMMR). The AMMR is commercially available from Anybody Technology of Denmark. The generic three-dimensional bony anatomy model may simulate an average individual, e.g. an average 60 year old male, an average 40 year old female, etc. The generic three-dimensional bony anatomy model may be load tested in various simulations, e.g. running or walking, using, for example, the Anybody Modeling System, which is commercially available from Anybody Technology of Denmark. By load testing the generic three-dimensional bony anatomy model, generic implants may be designed for use with a variety of different patient anatomies.

Figures 10, 11:
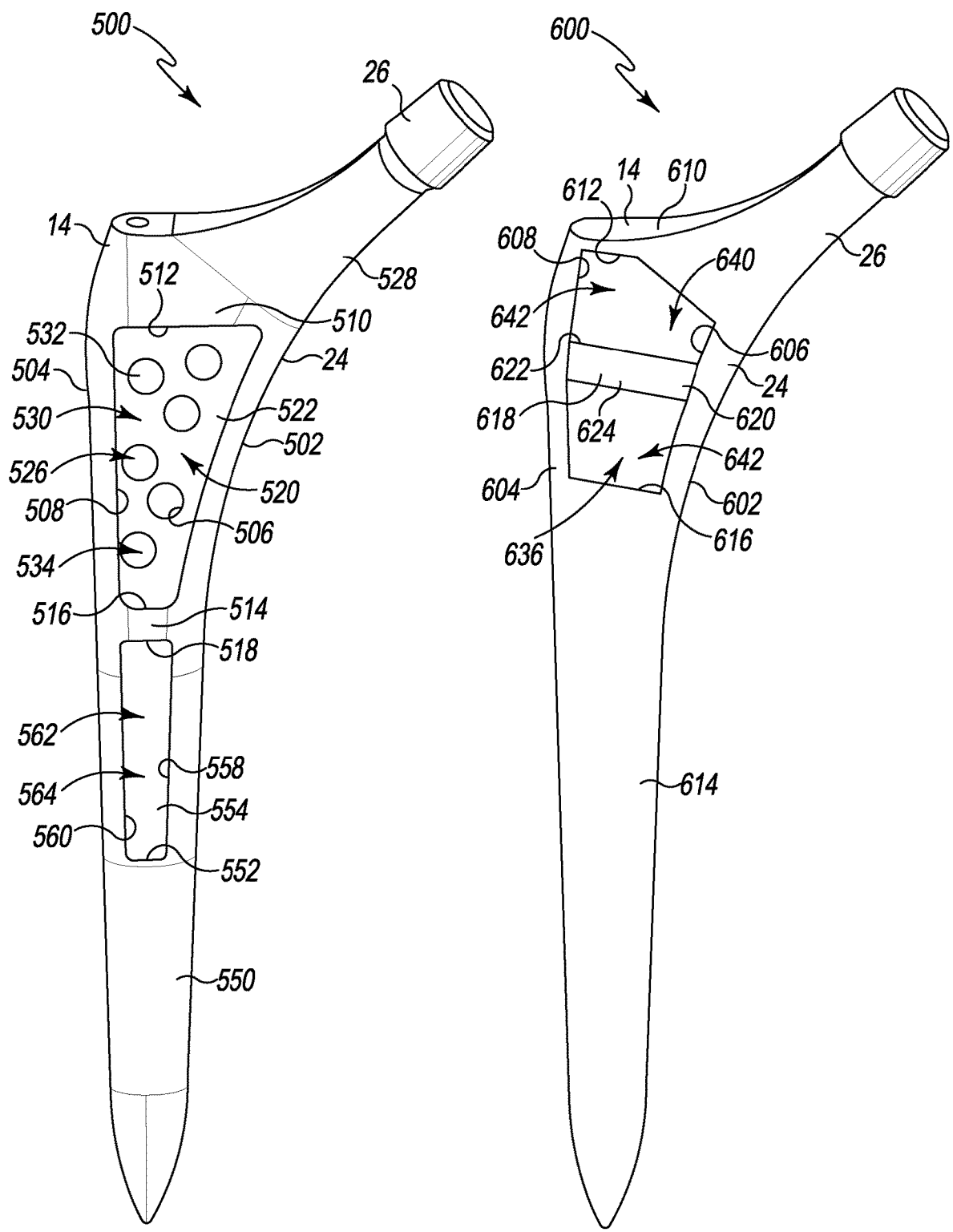
FIG. 10 is a side elevation view of another embodiment of a femoral orthopaedic prosthesis.
FIG. 11 is a side elevation view of yet another embodiment of a femoral orthopaedic prosthesis.

Referring now to FIG. 10, another embodiment of a femoral orthopaedic prosthesis (hereinafter implant 500) is shown. Although the implant 500 is illustratively a generic, non-patient specific implant, the implant 500 includes some of the same features as the implant 10, which are referenced using the same reference numbers. The implant 500 includes the head component 12 and the elongated stem component 14. The head component 12 is configured to engage a patient's natural acetabulum (not shown) or a prosthetic acetabular cup implanted into the patient's pelvic bone. The stem component 14 includes the core 24 having the neck 26, which configured to be coupled to the head component 12.

The core 24 includes a medial beam 502 and a lateral beam 504 spaced apart from the medial beam 502. The medial beam 502 includes a sidewall 506, and the lateral beam 502 includes a sidewall 508. A proximal section 510 having a sidewall 512 extends between the medial beam 502 and the lateral beam 504. A central beam 514 having a proximal sidewall 516 and a distal sidewall 518 extends between the medial beam 502 and the lateral beam 504. The central beam 514 is spaced apart from the proximal section 510. A cross-beam 520 extends between the medial beam 502 and the lateral beam 504. The cross-beam 520 also extends between the proximal section 510 and the central beam 514. The cross-beam 520 includes a posterior bottom wall 522 that extends between the sidewall 506 of the medial beam 502 and the sidewall 508 of the lateral beam 504. The posterior bottom wall 522 also extends between the sidewall 512 of the proximal section 510 and the sidewall 516 of the central beam 514.

An opening 526 is formed in a posterior surface 528 of the implant 500. The sidewall 506 of the medial beam 502, the sidewall 508 of the lateral beam 504, the sidewall 516 of the central beam 514, and the sidewall 512 of the proximal section 510 extend from the opening 526 to the posterior bottom wall 522 to define a proximal posterior notch 530 in the implant 500. Although the implant 500 is described with respect to the proximal posterior notch 530, it should be appreciated that the implant 500 also includes a proximal anterior notch (not shown) defined at least partially by an anterior bottom wall (not shown) of the cross-beam 520. A plurality of openings 532 are formed in the posterior bottom wall 522. A bore 534 extends from each opening 532 to another opening (not shown) formed in the anterior bottom wall. The illustrated embodiment includes six bores 534; however, it will be appreciated that, per routine 250, the implant 500 may have any number of bores 534. The bores 534, the posterior notch 530 and the anterior aperture are configured to be filled with porous foam, as described above.

The implant 500 also includes a distal section 550 having a sidewall 552 that extends between the medial beam 502 and the lateral beam 504. The distal section 550 is spaced apart from the central beam 514. A cross-beam 554 extends between the medial beam 502 and the lateral beam 504. The cross-beam 554 also extends between the distal section 550 and the central beam 514. The cross-beam 554 includes a posterior bottom wall 556 that extends between a sidewall 558 of the medial beam 502 and a sidewall 560 of the lateral beam 504. The posterior bottom wall 556 also extends between the sidewall 552 of the distal section 550 and the sidewall 518 of the central beam 514.

An opening 564 is formed in the posterior surface 528. The sidewall 558 of the medial beam 502, the sidewall 560 of the lateral beam 504, the sidewall 518 of the central beam 514, the sidewall 552 of the distal section 550 extend from the opening 564 to the posterior bottom wall 556 to define a distal posterior notch 562 in the implant 500. Although the implant 500 is described with respect to the distal posterior notch 562, it should be appreciated that the implant 500 also includes a distal anterior notch (not shown) defined at least partially by an anterior bottom wall (not shown) of the cross-beam 554.

Referring now to FIG. 11, another embodiment of a femoral orthopaedic prosthesis (hereinafter implant 600) is shown. The implant 600 includes some of the same features as the implants 10, 500 which are referenced using the same reference numbers. The implant 600 includes the head component 12 and the elongated stem component 14. The head component 12 is configured to engage a patient's natural acetabulum (not shown) or a prosthetic acetabular cup implanted into the patient's pelvic bone. The stem component 14 includes the core 24 having the neck 26, which configured to be coupled to the head component 12.

The core 24 includes a medial beam 602 and a lateral beam 604 spaced apart from the medial beam 602. The medial beam 602 includes a sidewall 606, and the lateral beam 604 includes a sidewall 608. A proximal section 610 having a sidewall 612 extends between the medial beam 602 and the lateral beam 604. A distal section 614 having a sidewall 616 extends between the medial beam 602 and the lateral beam 604. The distal section 614 is spaced apart from the proximal section 610. A cross-beam 618 extends between the medial beam 602 and the lateral beam 604. The cross-beam 618 includes a posterior bottom wall 620 that extends between the sidewall 606 of the medial beam 602 and the sidewall 608 of the lateral beam 604. The cross-beam 618 also includes a proximal sidewall 622 and a distal sidewall 624 extending between the sidewall 606 of the medial beam 602 and the sidewall 608 of the lateral beam 604.

An opening 636 is formed in a posterior surface 638 of the implant 600. The sidewall 606 of the medial beam 602 and the sidewall 608 of the lateral beam 604 extend from the opening 636 to the posterior bottom wall 620 to define a posterior aperture 640 in the implant 600. The sidewall 616 of the distal section 614 and the sidewall 612 of the proximal section 610 also extend from the opening 636 and cooperate to define the posterior aperture 640. Although the implant 600 is described with respect to the posterior aperture 640, it should be appreciated that the implant 600 also includes an anterior aperture (not shown) defined at least partially by an anterior bottom wall (not shown) of the cross-beam 618. When not intersected by the cross-beam 618, the posterior aperture 640 and the anterior aperture cooperate to define openings 642 through the implant.

Figures 12, 13:
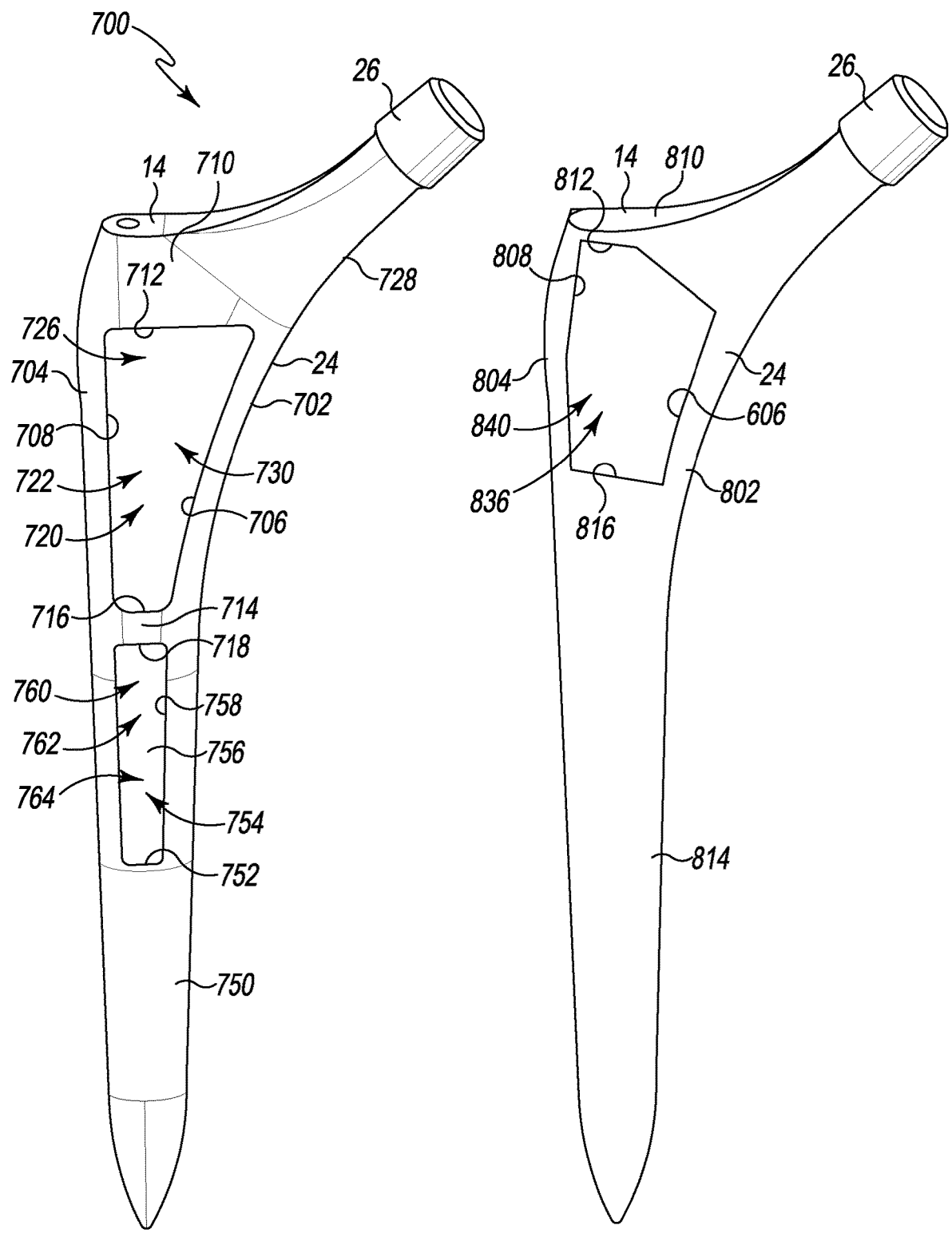
FIG. 12 is a side elevation view of a further embodiment of a femoral orthopaedic prosthesis.
FIG. 13 is a side elevation view of yet a further embodiment of a femoral orthopaedic prosthesis.

Referring now to FIG. 12, a femoral orthopaedic prosthesis (hereinafter implant 700) is shown. The implant 700 includes some of the same features as the implants 10, 500, 600, which are referenced using the same reference numbers. The implant 700 includes the head component 12 and the elongated stem component 14. The head component 12 is configured to engage a patient's natural acetabulum (not shown) or a prosthetic acetabular cup implanted into the patient's pelvic bone. The stem component 14 includes the core 24 having the neck 26, which configured to be coupled to the head component 12.

The core 24 includes a medial beam 702 and a lateral beam 704 spaced apart from the medial beam 702. The medial beam 702 includes a sidewall 706, and the lateral beam 702 includes a sidewall 708. A proximal section 710 having a sidewall 712 extends between the medial beam 702 and the lateral beam 704. A central beam 714 having a proximal sidewall 716 and a distal sidewall 718 extends between the medial beam 702 and the lateral beam 704. The central beam 714 is spaced apart from the proximal section 710. A cross-beam 720 extends between the medial beam 702 and the lateral beam 704. The cross-beam 720 also extends between the proximal section 710 and the central beam 714. The cross-beam 720 includes a posterior bottom wall 722 that extends between the sidewall 706 of the medial beam 702 and the sidewall 708 of the lateral beam 704. The posterior bottom wall 722 also extends between the sidewall 712 of the proximal section 710 and the proximal sidewall 716 of the central beam 714.

An opening 726 is formed in a posterior surface 728 of the implant 700. The sidewall 706 of the medial beam 702, the sidewall 708 of the lateral beam 704, the proximal sidewall 716 of the central beam 714, and the sidewall 712 of the proximal section 710 extend from the opening 726 to the posterior bottom wall 722 to define a proximal posterior notch 730 in the implant 700. Although the implant 700 is described with respect to the proximal posterior notch 730, it should be appreciated that the implant 700 also includes a proximal anterior notch (not shown) defined at least partially by an anterior bottom wall (not shown) of the cross-beam 720.

The implant 700 also includes a distal section 750 having a sidewall 752 that extends between the medial beam 702 and the lateral beam 704. The distal section 750 is spaced apart from the central beam 714. A cross-beam 754 extends between the medial beam 702 and the lateral beam 704. The cross-beam 754 also extends between the distal section 750 and the central beam 714. The cross-beam 754 includes a posterior bottom wall 756 that extends between a sidewall 758 of the medial beam 702 and a sidewall 762 of the lateral beam 704. The posterior bottom wall 756 also extends between the sidewall 752 of the distal section 750 and the distal sidewall 178 of the central beam 714.

An opening 760 is formed in the posterior surface 728. The sidewall 758 of the medial beam 702, the sidewall 762 of the lateral beam 704, the distal sidewall 178 of the central beam 714, the sidewall 752 of the distal section 750 extend from the opening 760 to the posterior bottom wall 756 to define a distal posterior notch 764 in the implant 700. Although the implant 700 is described with respect to the distal posterior notch 764, it should be appreciated that the implant 700 also includes a distal anterior notch (not shown) defined at least partially by an anterior bottom wall (not shown) of the cross-beam 754.

Referring now to FIG. 13, another embodiment of a femoral orthopaedic prosthesis (hereinafter implant 800) is shown. The implant 800 includes some of the same features as the implants 10, 500, 600, 700, which are referenced using the same reference numbers. The implant 800 includes the head component 12 and the elongated stem component 14. The head component 12 is configured to engage a patient's natural acetabulum (not shown) or a prosthetic acetabular cup implanted into the patient's pelvic bone. The stem component 14 includes the core 24 having the neck 26, which configured to be coupled to the head component 12.

The core 24 includes a medial beam 802 and a lateral beam 804 spaced apart from the medial beam 702. The medial beam 802 includes a sidewall 806, and the lateral beam 804 includes a sidewall 808. A proximal section 810 having a sidewall 812 extends between the medial beam 802 and the lateral beam 804. A distal section 814 having a sidewall 816 extends between the medial beam 802 and the lateral beam 804. The distal section 814 is spaced apart from the proximal section 810. An opening 836 is formed in a posterior surface 838 of the implant 800. The sidewall 806 of the medial beam 802, the sidewall 808 of the lateral beam 804, the sidewall 816 of the distal section 814, and the sidewall 812 of the proximal section 810 extend from the opening 836 to an opening formed in an anterior surface (not shown) of the implant 800 to define an aperture 840 in the implant 800.

Figure 14:
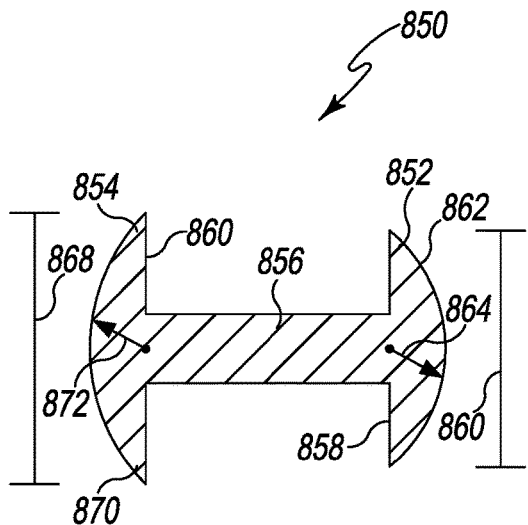
FIG. 14 is a plan cross-sectional view of an embodiment of a femoral orthopaedic prosthesis.

Referring now to FIG. 14, a transverse cross-section of another femoral orthopaedic prosthesis (hereinafter implant 850) is shown. The cross-section of the implant 850 is similar to the cross-section of the implant 10 shown in FIG. 3 and is taken at a similar point along the elongated stem of the implant 850. The implant 850 includes a medial beam 852 spaced apart from a lateral beam 854. A cross-beam 856 extends between the medial beam 852 and the lateral beam 854. The medial beam 852 includes a lateral surface 858 having a length 860. A curved medial surface 862 having a radius 864 extends medially from the lateral surface 858. The lateral beam 854 includes a medial surface 866 having a length 868 that is less than the length 860 of the lateral surface 858 of the medial beam 852. A curved lateral surface 870 having a radius 872 extends from the medial surface 866. The radius 872 is less than the radius 864. In the illustrative embodiment, the structure of the implant 850 matches the structure of the implant 10 other than the configuration of the beams 852, 854, 856.

Figure 15:
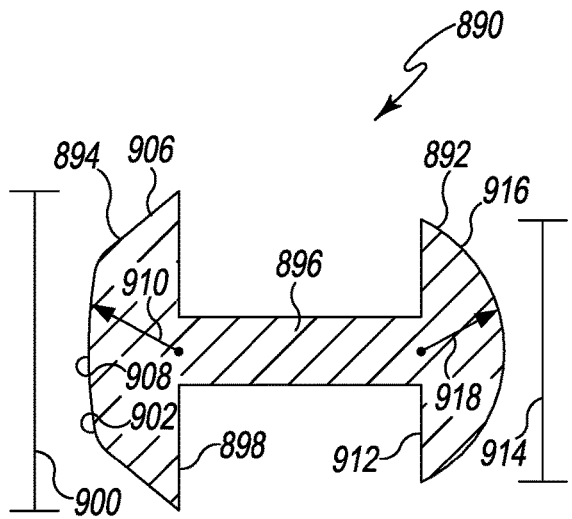
FIG. 15 is another plan cross-sectional view of an embodiment of a femoral orthopaedic prosthesis.

Referring now to FIG. 15, a transverse cross-section of another femoral orthopaedic prosthesis (hereinafter implant 890) is shown. The cross-section of the implant 890 is similar to the cross-section of the implant 10 shown in FIG. 3 and is taken at a similar point along the elongated stem of the implant 890. The implant 890 includes a medial beam 892 spaced apart from a lateral beam 894. A cross-beam 896 extends between the medial beam 892 and the lateral beam 894. The lateral beam 894 includes a medial surface 898 having a length 900. A lateral surface 902 extends from the medial surface 898. The lateral surface 902 includes a substantially linear anterior end surface 904 and a substantially linear posterior end surface 906 extending from the medial surface 898. A curved surface 908 having a radius 910 extends between the anterior end surface 904 and the posterior end surface 906. The medial beam 892 includes a lateral surface 912 having a length 914 that is less than the length 900 of the medial surface 898 of the lateral beam 894. A curved medial surface 916 having a radius 918 extends from the lateral surface 912. The radius 918 is less than the radius 910. In the illustrative embodiment, the structure of the implant 890 matches the structure of the implant 10 other than the configuration of the beams 892, 894, 896.

Figure 16:
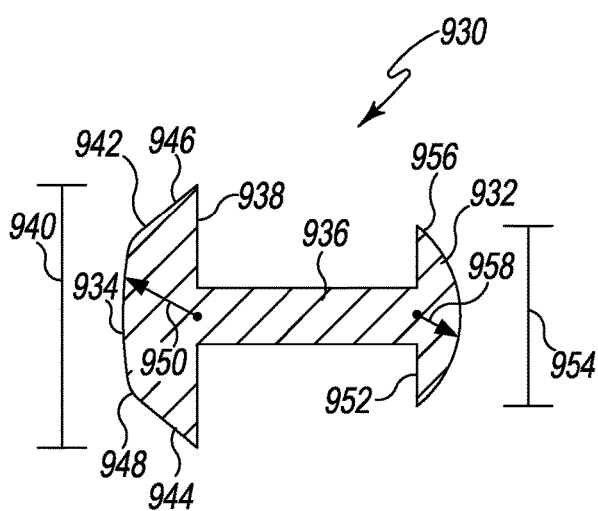
FIG. 16 is another plan cross-sectional view of another embodiment of a femoral orthopaedic prosthesis.

Referring now to FIG. 16, a transverse cross-section of another femoral orthopaedic prosthesis (hereinafter implant 930) is shown. The cross-section of the implant 930 is similar to the cross-section of the implant 10 shown in FIG. 3 and is taken at a similar point along the elongated stem of the implant 930. The implant 930 includes a medial beam 932 spaced apart from a lateral beam 934. A cross-beam 936 extends between the medial beam 932 and the lateral beam 934. The lateral beam 934 includes a medial surface 938 having a length 940. A lateral surface 942 extends from the medial surface 938. The lateral surface 942 includes a substantially linear anterior end surface 944 and a substantially linear posterior end surface 946 extending from the medial surface 938. A curved surface 948 having a radius 950 extends between the anterior end surface 944 and the posterior end surface 946. The medial beam 932 includes a lateral surface 952 having a length 954 that is less than the length 940 of the medial surface 938 of the lateral beam 934. The length 954 is also less than the length 914 of the lateral surface 912 of the implant 890, shown in FIG. 15. A curved medial surface 956 having a radius 958 extends from the lateral surface 952. The radius 958 is less than the radius 950. The radius 958 is also less than the radius 918 of the curved medial surface 916 of the implant 890, shown in FIG. 15. In the illustrative embodiment, the structure of the implant 930 matches the structure of the implant 10 other than the configuration of the beams 932, 934, 936.

Figure 17:
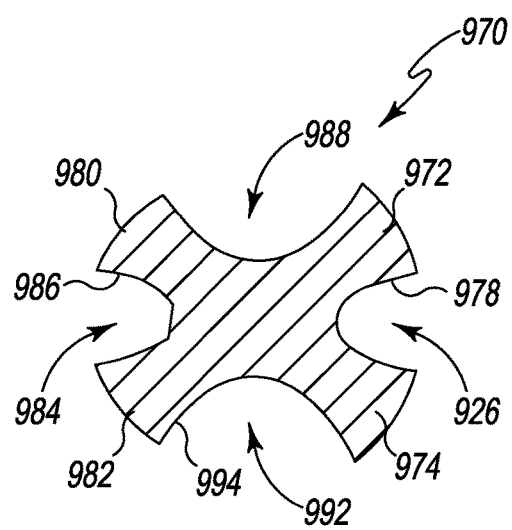
FIG. 17 is a plan cross-sectional view of another embodiment of a femoral orthopaedic prosthesis.

Referring now to FIG. 17, a transverse cross-section of another femoral orthopaedic prosthesis (hereinafter implant 970) is shown. The cross-section of the implant 970 is similar to the cross-section of the implant 10 shown in FIG. 3 and is taken at a similar point along the elongated stem of the implant 970. The implant 970 includes a pair of spaced apart medial beams 972 and 974. The medial beams 972 and 974 are separated by an arcuate opening 976 defined by a sidewall 978 that extends from the beam 972 to the beam 974. The implant 970 also includes a pair of spaced apart lateral beams 980 and 982. The lateral beams 980 and 982 are separated by an arcuate opening 984 defined by a sidewall 986 that extends from the beam 980 to the beam 982. The medial beam 972 is separated from the lateral beam 980 by an arcuate opening 988 that is defined by a sidewall 990 that extends from the medial beam 972 to the lateral beam 980. The medial beam 974 is separated from the lateral beam 982 by an arcuate opening 992 that is defined by a sidewall 994 that extends from the medial beam 974 to the lateral beam 982. Collectively, the medial beams 972, 974 and the lateral beams 980, 982 are formed as a monolithic substantially X-shaped structure. In the illustrative embodiment, the structure of the implant 970 matches the structure of the implant 10 other than the configuration of the beams 972, 974, 980, 982.

Although the embodiments above are described with respect to a total hip replacement, the routine and beam configurations described above may also be utilized with in other joint arthroplasties, e.g. total knee replacement or total shoulder replacement.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A femoral orthopaedic prosthesis, comprising:
  a metallic core extending from a proximal end to a distal tip, the metallic core including (i) a neck that is positioned at the proximal end and is configured to receive a prosthetic femoral ball, and (ii) an elongated stem extending distally from the neck to the distal tip, and
  porous foam coupled to the metallic core,
  wherein the stem includes:
    a proximal section extending distally from the neck,
    a distal section extending proximally from the distal tip,
    a medial beam having a proximal end connected to the proximal section, a distal end connected to the distal section, an anterior side, and a posterior side,
    a lateral beam spaced apart from the medial beam and having a proximal end connected to the proximal section, a distal end connected to the distal section, an anterior side, and a posterior side, and
    a cross-beam having a first end connected to an inner wall of the medial beam, a second end connected to an inner wall of the lateral beam, an anterior side that extends from the first end to the second end and that is offset posteriorly relative to the anterior sides of the medial beam and the lateral beam, and a posterior side that extends from the first end to the second end and is offset anteriorly relative the posterior sides of the medial beam and the lateral beam; and a central beam that extends between the medial beam and the lateral beam, wherein the central beam includes an anterior surface that is substantially planar with the anterior sides of the medial and lateral beams and a posterior surface that is substantially planar with posterior sides of the medial and lateral beams, wherein a first portion of the porous foam is positioned in an anterior notch that is defined between the proximal section, the distal section, the inner walls of the medial and lateral beams, and the anterior side of the cross-beam and wherein the first portion covers the anterior side of the cross-beam, and wherein a second portion of the porous foam is positioned in a posterior notch that is defined between the proximal section, the distal section, the inner walls of the medial and lateral beams, and the posterior side of the cross-beam and wherein the second portion of the porous foam covers the posterior side of the cross-beam, and wherein the central beam separates each of the anterior notch and the posterior notch into respective first and second sections.

2. The femoral orthopaedic prosthesis of claim 1, further comprising an opening defined through the cross-beam.

3. The femoral orthopaedic prosthesis of claim 2, wherein the porous foam extends through the opening defined through the cross-beam.

4. The femoral orthopaedic prosthesis of claim 1, wherein the porous foam includes an anterior surface that is substantially planar with an anterior surface of the stem, and a posterior surface that is substantially planar with a posterior surface of the stem.

5. The femoral orthopaedic prosthesis of claim 1, wherein the medial beam defines a portion of a medial edge of the stem, and the lateral beam defines a portion of a lateral edge of the stem.

6. The femoral orthopaedic prosthesis of claim 1, wherein:
the cross-beam includes a plurality of cross-beams that extend between the pair of spaced-apart beams, and each cross-beam extends obliquely relative to the other cross-beams of the plurality of cross-beams.

7. The femoral orthopaedic prosthesis of claim 1, further comprising a prosthetic femoral ball including a distal opening sized to receive the proximal end of the metallic core.

8. The femoral orthopaedic prosthesis of claim 1, wherein the porous foam has an elastic modulus of no greater than 20 Gigapascals (GPa).

9. The femoral orthopaedic prosthesis of claim 8, wherein the porous foam has an elastic modulus in the range of 10 Gigapascals (GPa) to 20 Gigapascals (GPa).

10. The femoral orthopaedic prosthesis of claim 8, wherein the porous foam has an elastic modulus of 10 Gigapascals (GPa).

11. The femoral orthopaedic prosthesis of claim 1, wherein the porous foam comprises a metallic foam matrix.

12. The femoral orthopaedic prosthesis of claim 11, wherein the porous foam comprises a titanium foam matrix.

13. The femoral orthopaedic prosthesis of claim 12, wherein the titanium foam matrix has an elastic modulus of approximately 10 Gigapascals (GPa).

14. The femoral orthopaedic prosthesis of claim 11, wherein the porous foam comprises a cobalt-chromium (CoCr) foam matrix.

15. The femoral orthopaedic prosthesis of claim 14, prosthesis of claim 1, wherein the cobalt-chromium (CoCr) foam matrix has an elastic modulus of 19 Gigapascals (GPa).

16. The femoral orthopaedic prosthesis of claim 1, wherein:
the cross-beam is a first cross-beam that cooperates to define the first section of the anterior and posterior notches, and
the stem includes a second cross-beam that cooperates to define the second section of the anterior and posterior notches.

* * * * *